(12) United States Patent
Arcaro et al.

(10) Patent No.: US 10,155,104 B2
(45) Date of Patent: Dec. 18, 2018

(54) VALVE ASSEMBLY FOR MEDICAL PROCEDURES

(71) Applicant: W. L. Gore & Associates, Inc., Newark, DE (US)

(72) Inventors: David J. Arcaro, Flagstaff, AZ (US); James L. Goepfrich, Flagstaff, AZ (US); William Wilkie, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 15/077,610

(22) Filed: Mar. 22, 2016

(65) Prior Publication Data

US 2016/0354598 A1 Dec. 8, 2016

Related U.S. Application Data

(62) Division of application No. 12/477,470, filed on Jun. 3, 2009, now Pat. No. 9,314,605.

(60) Provisional application No. 61/058,744, filed on Jun. 4, 2008.

(51) Int. Cl.

| *A61M 39/22* | (2006.01) |
| *A61M 39/06* | (2006.01) |
| *B33Y 10/00* | (2015.01) |
| *B33Y 80/00* | (2015.01) |
| *B29L 31/00* | (2006.01) |
| *B29C 64/135* | (2017.01) |

(52) U.S. Cl.
CPC ...... *A61M 39/228* (2013.01); *A61M 39/0613* (2013.01); *A61M 2039/0673* (2013.01); *B29C 64/135* (2017.08); *B29L 2031/7546* (2013.01); *B33Y 10/00* (2014.12); *B33Y 80/00* (2014.12); *Y10T 29/49764* (2015.01); *Y10T 29/49826* (2015.01); *Y10T 29/49904* (2015.01); *Y10T 29/49925* (2015.01)

(58) Field of Classification Search
CPC ............ A61M 39/228; A61M 39/0613; A61M 2039/0673; B29C 67/0066; B33Y 80/00; B33Y 10/00; B29L 2031/7546; Y10T 29/49925; Y10T 29/49764; Y10T 29/49904; Y10T 29/49826
See application file for complete search history.

(56) References Cited

U.S. PATENT DOCUMENTS

| 4,701,160 A | 10/1987 | Lindsay et al. |
| 5,071,411 A | 12/1991 | Hillstead |
| 5,238,984 A | 8/1993 | Wallquist et al. |
| 5,329,921 A | 7/1994 | Socaris et al. |
| 5,634,911 A | 6/1997 | Hermann |

(Continued)

FOREIGN PATENT DOCUMENTS

| GB | 1514019 | 6/1978 |
| JP | S62292170 | 12/1987 |

(Continued)

*Primary Examiner* — John C Hong (57) ABSTRACT

The invention relates to a valve used in medical procedures. More specifically the invention relates to an introducer sheath valve used in minimally invasive and conventional surgical procedures. The valve may accommodate a wide range of surgical implement diameters, shapes, and multiple implements without imposing the high frictional forces of known valves.

12 Claims, 9 Drawing Sheets

(56) References Cited

U.S. PATENT DOCUMENTS

| | | | |
|---|---|---|---|
| 6,488,653 B1 * | 12/2002 | Lombardo | A61M 25/1002 604/101.01 |
| 7,049,380 B1 | 5/2006 | Chang et al. | |
| 7,390,317 B2 | 6/2008 | Taylor et al. | |
| 8,079,986 B2 | 12/2011 | Taylor et al. | |
| 2007/0012624 A1 | 1/2007 | Bacino et al. | |
| 2008/0053892 A1 | 3/2008 | Bacino et al. | |
| 2008/0109028 A1 | 5/2008 | Styre | |

FOREIGN PATENT DOCUMENTS

| | | |
|---|---|---|
| WO | WO-1999011308 | 3/1999 |
| WO | WO-2004045386 | 6/2004 |
| WO | WO-2004093937 | 11/2004 |
| WO | WO-2008021006 | 2/2008 |

* cited by examiner

VALVE ASSEMBLY FOR MEDICAL PROCEDURES

CROSS REFERENCE TO RELATED APPLICATIONS

This application is a divisional of U.S. patent application Ser. No. 12/477,470, filed Jun. 3, 2009, entitled VALVE ASSEMBLY FOR MEDICAL PROCEDURES, which claims priority to Provisional Application No. 61/058,744, filed Jun. 4, 2008, entitled INTRODUCER SHEATH VALVE.

BACKGROUND OF THE INVENTION

Field of the Invention

The invention relates to a valve assembly for medical procedures.

Discussion of the Related Art

Valve assemblies are used in many medical procedures. More specifically, introducer sheath valves are used in a wide variety of minimally invasive and conventional surgical procedures. For example, laparoscopic and arthroscopic surgical procedures are often performed through trocar assemblies, which include introducer sheath valves.

Current introducer sheath valves generally fall into two basic categories: passive and active. A passive introducer sheath valve generally relies on the deformation of a resilient sealing body by the implement inserted through the valve to form the desired fluid tight seal. Active valves include a mechanism that moves a sealing body into contact with the traversing implement. An example of an active valve would be constructed of a housing and a tubular resilient valve carried within the housing. This valve requires a means for varying the pressure in the space within the housing but outside of the tubular valve in order to urge the resilient valve to collapse inwardly to seal around the implement.

Another example of an active valve is constructed of an elastomeric sealing body, which will maintain hemostasis by contacting a surgical implement traversing the valve over a very small contact area. The orifice is formed in the thin elastomeric membrane, which extends radially inward from a torroidal balloon having a relatively rigid outer rim and a flexible inner portion. In this example, a vacuum is applied within the torroidal balloon to pull the elastomeric membrane radially outward for implement insertion. Sealing around the implement is actuated by applying a positive pressure within the torroidal balloon expanding the balloon radially inward to block access through the valve.

While these and other valve designs are fairly tolerant of various diameters of surgical implements, all of the currently available valves have significant limitation as to the variation in diameter, variation in shape of implement and how many implements which can pass through the valve without damaging it and with optimal sealing properties. For these reasons, it would be desirable to provide improved introducer sheath valves for use in endovascular, laparoscopic and other surgical procedures. Such valves would preferably seal over a wide range of surgical implement diameters, shapes, and multiple implements without imposing the high frictional forces of known valves, regardless of cross-sectional size or shape of the surgical implement traversing the valve.

Although specifically discussed as an introducer sheath valve, the invention encompasses other applications such as bariatric port access, medical injection port, vascular access port, valve for insertion sites such as feeding tubes or dialysis access port, etc.

SUMMARY OF THE INVENTION

A first embodiment provides an introducer sheath valve having an outer tube and an inner tube comprised of a porous substrate with a pressurizable space formed between the inner surface of the outer tube and the outer surface of the inner tube.

A further embodiment provides an introducer sheath valve having an outer tube and an inner tube with a thickness of about 0.0025 mm to about 1 mm with a pressurizable space formed between the inner surface of the outer tube and the outer surface of the inner tube.

An additional embodiment provides an introducer sheath valve having an outer tube and an inner tube comprised of ePTFE (expanded polytetrafluoroethylene) with a pressurizable space formed between the inner surface of the outer tube and the outer surface of the inner tube.

Additional features and advantages of the invention will be set forth in the description or may be learned by practice of the invention. These features and other advantages of the invention will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The accompanying drawings are included to provide a further understanding of the invention and are incorporated in and constitute a part of this specification, illustrate embodiments of the invention, and together with the description serve to explain the principles of the invention.

In the drawings.

DETAILED DESCRIPTION OF THE ILLUSTRATED EMBODIMENTS

A first embodiment comprises an introducer sheath valve constructed of an outer tube and an inner tube comprised of a porous substrate with a pressurizable space formed between the inner surface of the outer tube and the outer surface of the inner tube.

Figure 1:
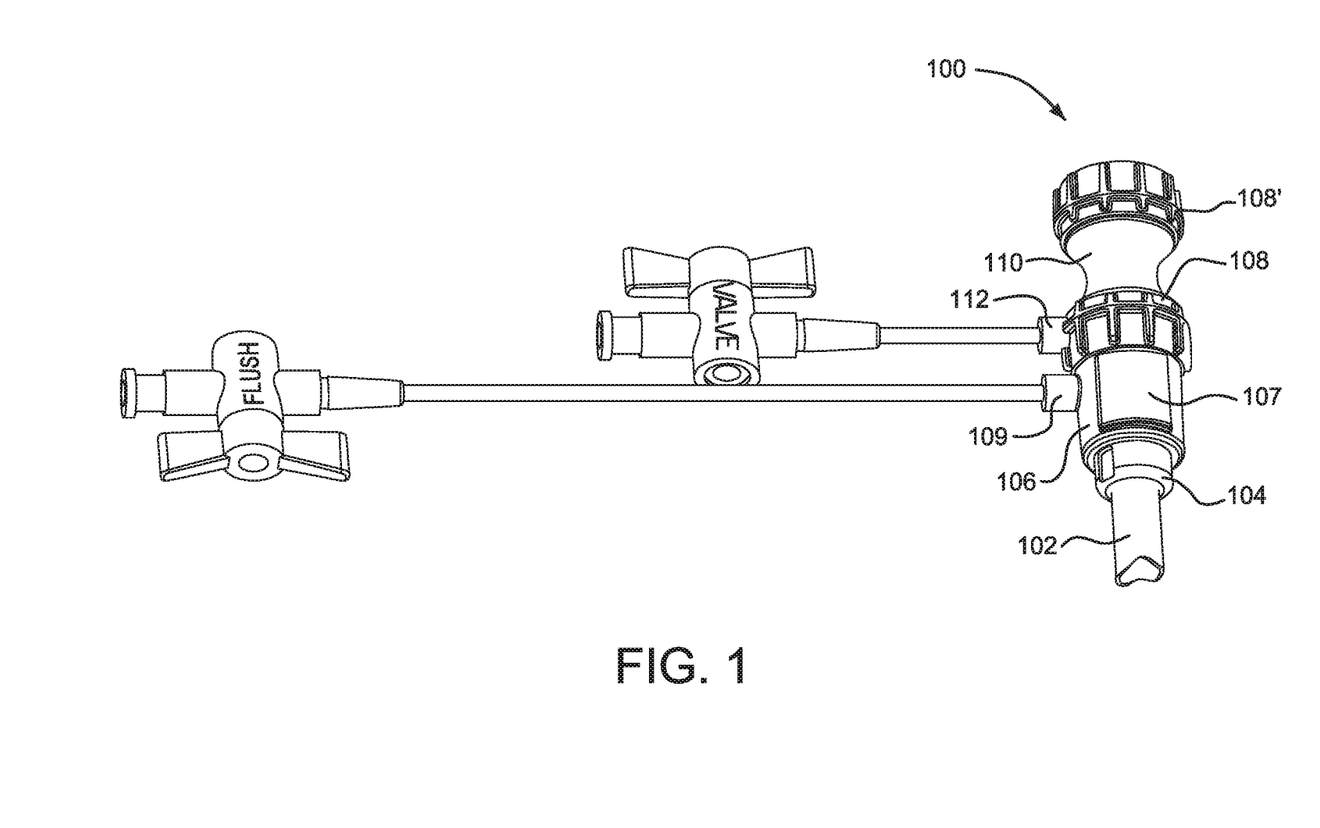
FIG. 1 is a perspective view of an introducer sheath which carries one embodiment of the introducer sheath valve.

FIG. 1 shows one embodiment of the introducer sheath valve 100. Introducer sheath valve 100 assembly may be attached to an introducer sheath 102. Sheath 102 may be manufactured of either fluorinated ethylene propylene (FEP) or extruded high density polyethylene or any other material with suitable biocompatible and mechanical properties. One of skill in the art can readily appreciate that there are a wide variety of potential materials that may be used to facilitate the present invention. Sheath 102 may be of any size but is preferably sized from about 12 to 26 Fr. On the proximal most end of the sheath 102 is the threaded adapter 104. The threaded adapter 104 may be manufactured of any biocompatible plastic or any biocompatible metal with suitable biocompatible and mechanical properties. Threaded adapter 104 may be attached to sheath 102 by a variety of means which include but are not limited to adhesives such as polyurethane adhesives, quick setting cyanoacrylate adhesives, or ultraviolet cured adhesives. Other means to attach threaded adapter 104 to sheath 102 may include ultrasonic welding, interference fit, thermal bond and insert molding. One of skill in the art can readily appreciate that there are a wide variety of potential means for attaching threaded adapter 104 to sheath 102. The distal end of the front fitting 106 may be attached to the proximal end of the threaded adapter 104. The threaded adapter 104, front fitting 106, snap ring 108 and snap ring 108' with fill port 112 may be manufactured of any biocompatible metal or plastic with suitable biocompatible and mechanical properties. Snap ring 108 and snap ring 108' with fill port 112 will be discussed further. Front fitting 106 may be attached to threaded adapter 104 with similar means as described in the attachment of threaded adapter 104 and sheath 102. Of the many features and attributes of front fitting 106, a few are outlined in the following description. Front fitting 106 is designed to enable a user to grip the device securely. Gripping may be aided by protrusions 107 on the lateral sides of the fitting 106. These protrusions 107 may be made of a similar material as that of the fitting 106 or may be made of a material with a high coefficient of friction or of a material more compliant than that of front fitting 106. These protrusions may also be made with grating, a roughening, a raised company logo or design, or striations in the surface in conjunction with the material listed above to further aid in the gripping of the device. These features on the surface of front fitting 106 may also be used to aid in gripping without the use gripping protrusions 107 and may be applied directly to the lateral surface of front fitting 106. Front fitting 106 also includes the feature of a flush port 109 with fitting. The function and use of a flush port 109 and fitting is commonly known in the arts.

Figure 2:
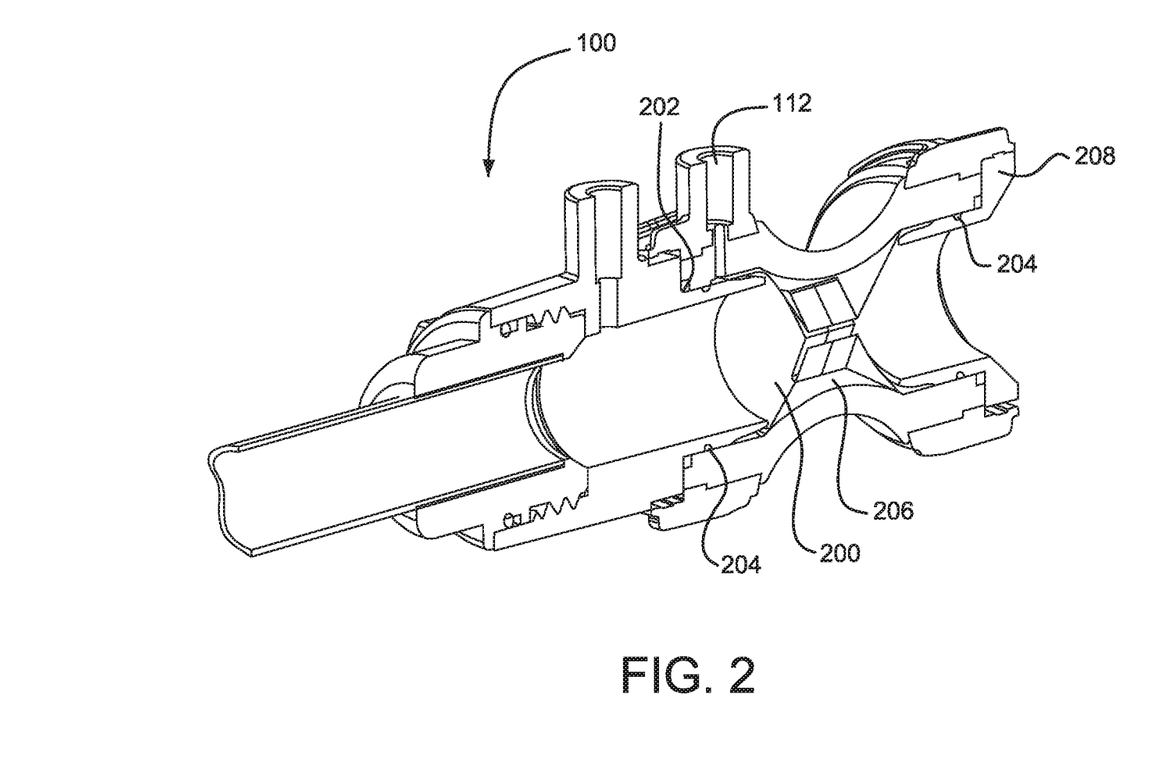
FIG. 2 is a cut away view of an introducer sheath which carries one embodiment of the introducer sheath valve.
Figure 3:
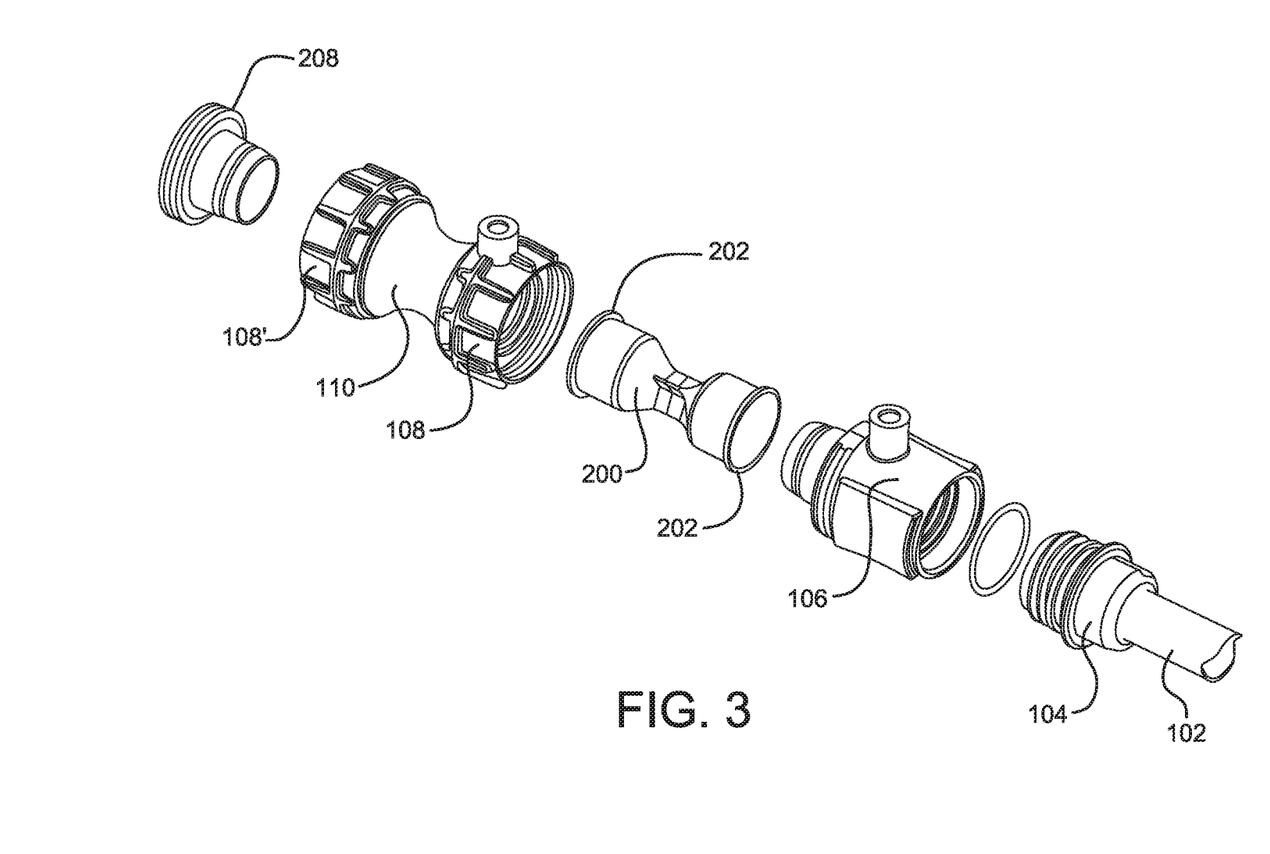
FIG. 3 is an expanded view of one embodiment of the introducer sheath valve.

As illustrated in FIG. 2, a cross-section of FIG. 1, and FIG. 3, an exploded view of FIG. 1, the outer sheath assembly may be constructed of a snap ring 108, an outer tube 110, and a snap ring 108' with fill port 112. As discussed previously, snap ring 108 and snap ring 108' with fill port 112 may be constructed of any biocompatible metal or plastic with suitable biocompatible and mechanical properties. Fill port 112 may be located at any point along snap ring 108 or 108'. Outer tube 110 preferably has the feature of a sealing lip 204. Sealing lip 204 aids in the secure fastening of snap ring 108 and snap ring 108' with fill port 112 to outer tube 110. Sealing lip 204 also provides a seal between tubes 110 and 200. Outer tube 110 may be attached to snap ring 108 and snap ring 108' with fill port 112 by a variety of methods. The preferable method for connecting the parts is that of insert molding as commonly practiced in the art. Other methods of attachment could include interference fit, adhesion or adhesives, ultrasonic welding and thermal bonding. Outer tube 110 may be constructed of any elastomer, latex or polycarbonate with desirable mechanical and biocompatible properties. In one embodiment, outer tube 110 comprises silicone and has a hourglass shape when not pressurized. When pressurized, the hourglass shape of outer tube 110 becomes distended to indicate a desirable pressure in the pressurizable space 206 (e.g., when the pressurizable space 206 is pressurized with at least one substance to a sufficient pressure to cause the inner tube 200 to collapse such that the pressure is sufficient to prevent back bleeding). Pressurizing methods and means will be described later. This feature of outer tube 110 enables the user of a device to easily and quickly identify the optimal pressure for the device.

FIGS. 2 and 3 also show an inner tube 200. Inner tube 200 may be formed with a ring 202 on each end of the inner tube 200. Inner tube 200 may be constructed of any very thin, strong, drape-able material such as ePTFE, fabrics, silk, or Kevlar® brand fiber. These materials may be used as a single layer construct or a multi-layer construct. In one embodiment, inner tube 200 can be formed of a thin porous substrate, ePTFE similar to that described in U.S. Patent Publication No. 2007/0012624 A1 or U.S. Patent Publication No. 2008/0053892 A1. This construct may be comprised of multiple layers of ePTFE that may be filled or imbibed with a polymer. The filling or imbibing polymer may be the same as the construct or may be a different polymer. One construct can be similar to that disclosed in U.S. Pat. No. 7,049,380. Porous substrate configurations will be further discussed with the description of FIGS. 5A-C, FIGS. 6A-C and FIGS. 7A-C.

FIGS. 2 and 3 illustrate rings 202 on the ends of inner tube 200. Rings 202 are used to create a stiff member to aid in attachment of inner tube 200 to front fitting 106 and to rear fitting 208. Rings 202 may be made of any material with desirable biocompatible and mechanical properties. Rings are preferably made of fluorinated ethylene propylene (FEP). Inner tube 200 with attached rings 202 may be inserted through the outer tube 110 and attached to the protruding end of front fitting 106. Snap ring 108 may then be attached to front fitting 106 with an adhesive, but other suitable attachment methods will suffice. The remaining free ring 202 may then be attached to the protrusion on rear fitting 208. Snap ring 108' with fill port 112 may then be snapped onto rear fitting 208. Methods for attaching snap ring 108' with fill port 112 and rear fitting 208 are similar to those describe previously. Materials used to manufacture both snap ring 108' with fill port 112 and rear fitting 208 have been discussed previously.

Figure 2A:
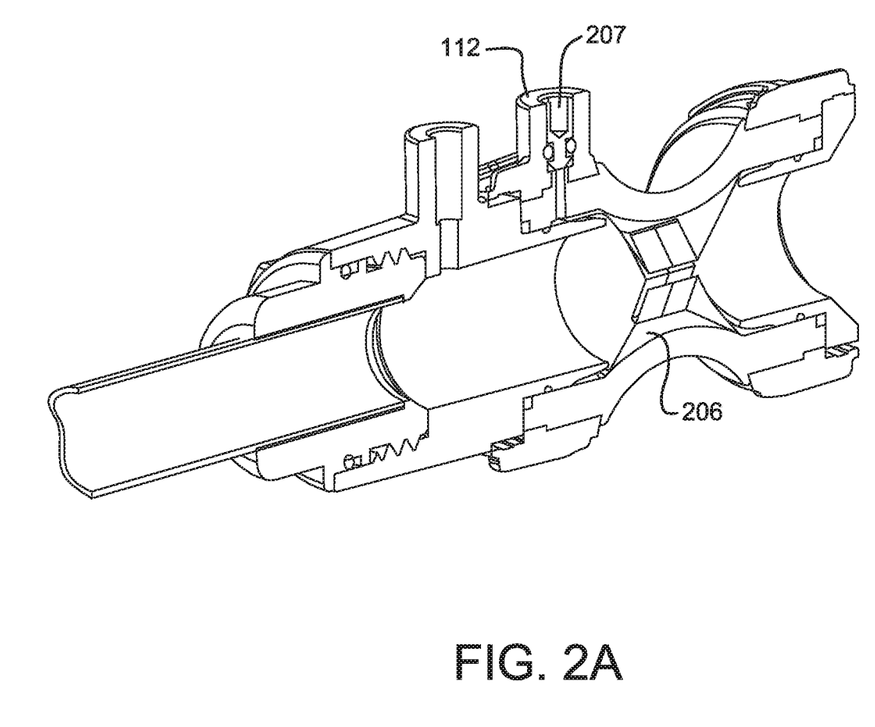
FIG. 2A is a cut away view of an introducer sheath which carries one embodiment of the introducer sheath valve.

FIG. 2A shows a embodiment in which pressurizable space 206 is filled prior to use and then fill port 112 is stopped with plug 207. This embodiment has largely the same components as shown in FIG. 2 with the addition of plug 207.

Figure 4:
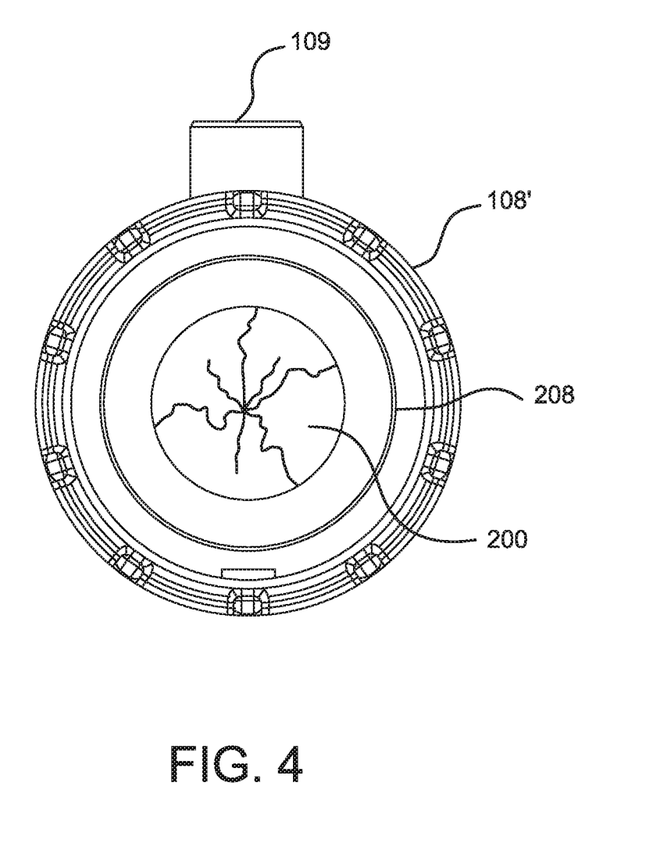
FIG. 4 is an end on view of one embodiment of the introducer sheath valve.

FIG. 4 illustrates an end on view of the device showing a collapsed inner tube 200. Snap ring 108' with fill port 112 has a feature that allows pressurizable space 206 to be filled to a sufficient pressure to cause the inner tube 200 to collapse. Pressurizable space 206 may be filled with any suitable material or materials. For example, pressurizable space 206 may be filled with one or more of the following substances: air, silicone, water, saline solution, low volatility biocompatible liquids, glycerin, propylene glycol, polyethylene glycol, compressible foam, elastomeric spheres, and crosslinked silicone gels.

Figure 5A:
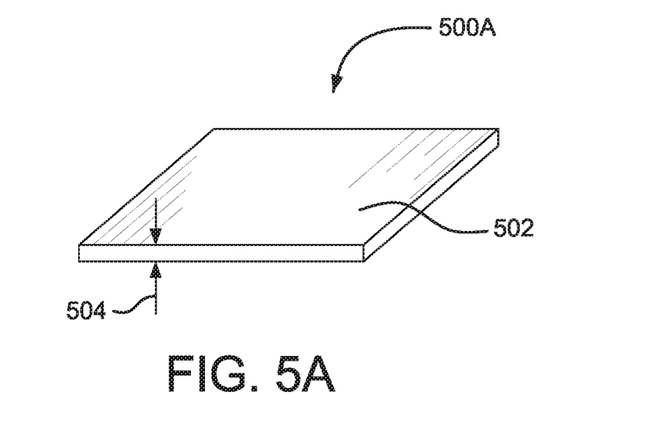
FIGS. 5A-C illustrate examples of a porous substrate.
Figure 5B:
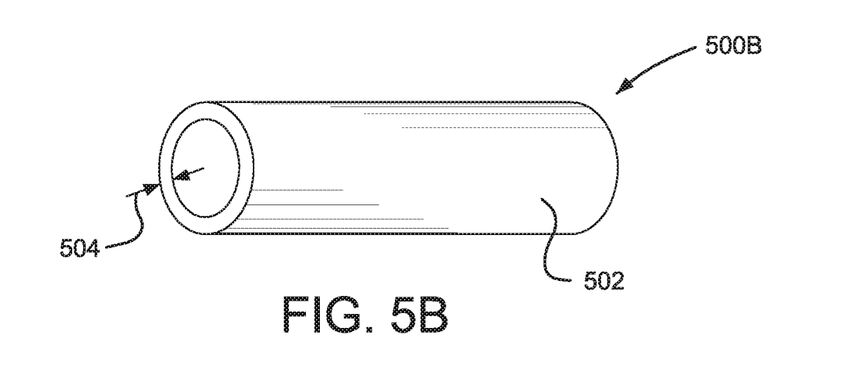
Figure 5C:
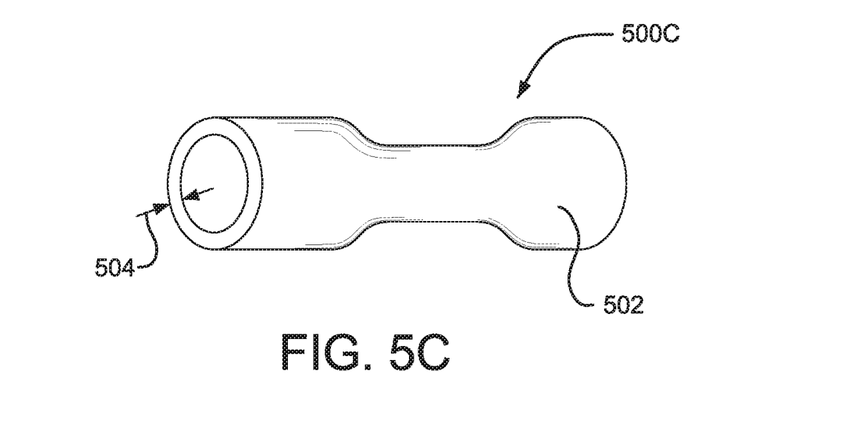

Shown in FIGS. 5A through C are perspective views of various porous substrates. Porous substrates can have various shapes or forms that are suited for particular applications.

FIG. 5A depicts a flat, planer substrate 500A having an outer surface 502 and a thickness 504. FIG. 5B is a cylindrical or tubular porous substrate 500B having an outer surface 502 and a thickness 504.

Porous substrates can have any form or shape, for example a flat planer shape, a cylindrical or tubular shape, or any other shapes as commonly known in the art. Dimensions of porous substrates can be varied according to a particular application. For example, the wall thickness 504 can be varied as well as the length, width, diameter etc. The particular dimensions can be varied along the substrate's length, width or across the substrates surface 502. For example, FIG. 5C shows a tubular porous substrate 500C where the diameter varies along the substrate length, forming a "dog-bone" shape.

Figure 6A:
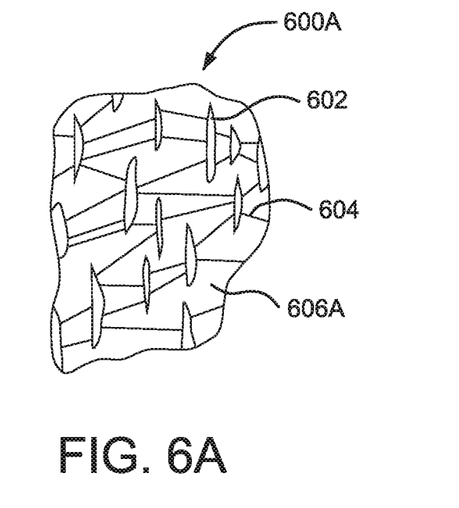
FIGS. 6A-C illustrate magnified examples of a surface of a porous substrate.
Figure 6B:
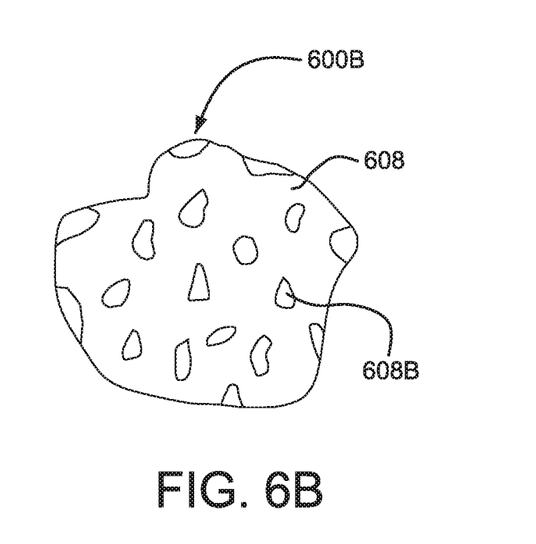
Figure 6C:
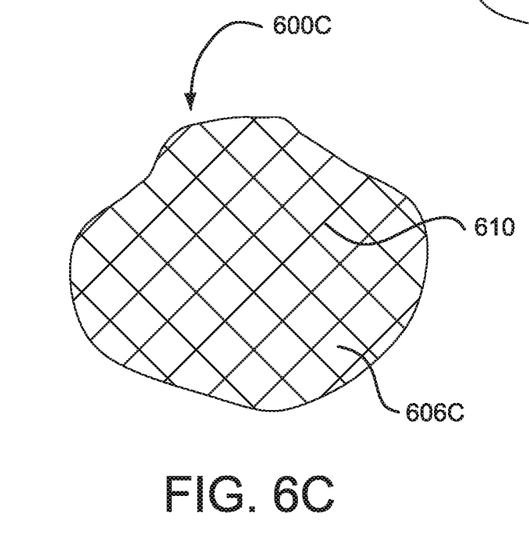

Porous substrates can be comprised of various materials such as ePTFE, fabrics, silk, Kevlar® brand fibers, or other materials known in the arts. A "porous substrate" is defined as a substrate having openings or pores which may be interconnected. Shown in FIGS. 6A through C are magnified partial views of the surface of a porous substrate. Shown in FIG. 6A is a porous substrate 600A having nodes 602 interconnected by fibrils 604. The openings or pores are shown as 606A. Porous substrates of this type would be similar to any expanded polymer. Similarly, shown in FIG. 6B is a porous substrate 600B comprised of a solid material 608 having openings or pores 606B. Porous substrates of this type would be similar to any biocompatible plastic. Openings or pores would be formed by mechanical or etching means. Other opening or pore forming means in plastics are commonly known in the art. Shown in FIG. 6C is a porous substrate 600C comprised of fibers or filaments 610, having openings or pores 606C. Porous substrates of this type would be similar to those of woven fabrics or those woven or formed of fibers.

Figure 7A:
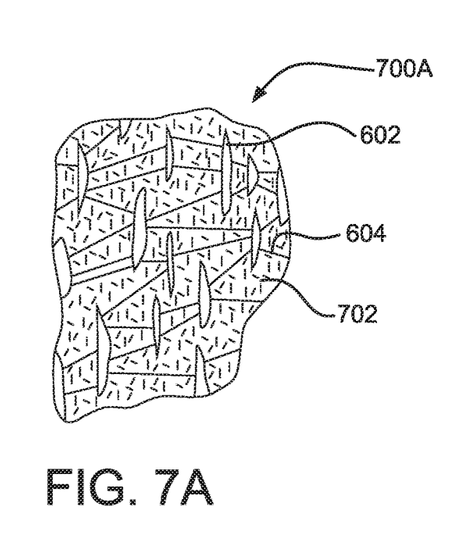
FIGS. 7A-C illustrate magnified examples of a surface of a porous substrate with a polymer filling openings or pores in the substrate.
Figure 7B:
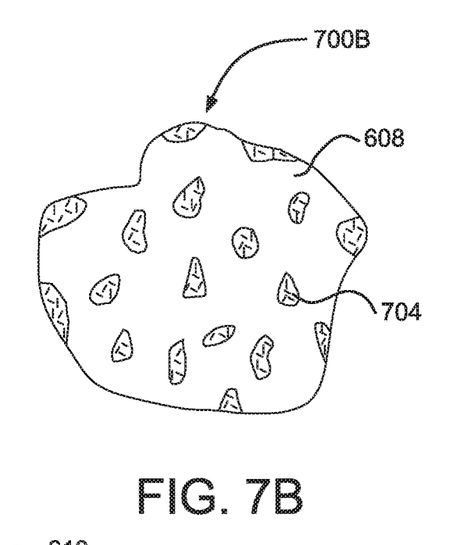
Figure 7C:
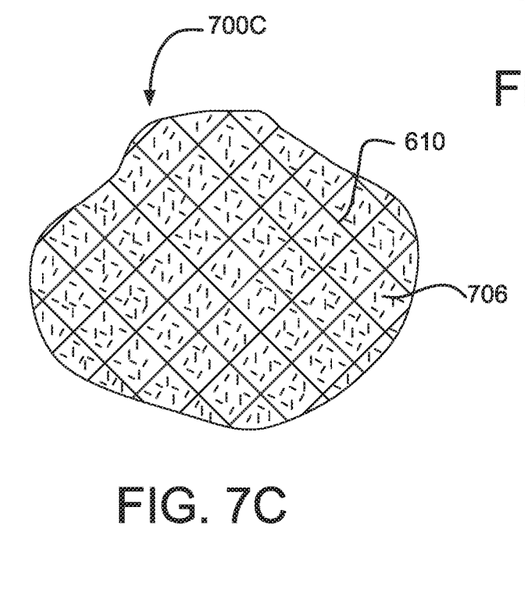

Porous substrates may be filled with a substance such as a polymer. The polymer used for filling openings or pores may be the same as the polymer of the substrate or of a different polymer. Shown in FIGS. 7A through C are magnified partial views of the surface of a porous substrate filled with a substance. FIG. 7A shows a porous substrate 700A having nodes 602 interconnected by fibrils 604 and filled pores 702. FIG. 7B shows a porous substrate 700B comprising a solid material 608 and filled pores 704. Shown in FIG. 7C is a porous substrate 700C having fibers 610 and filled openings or pores 706.

Figure 8:
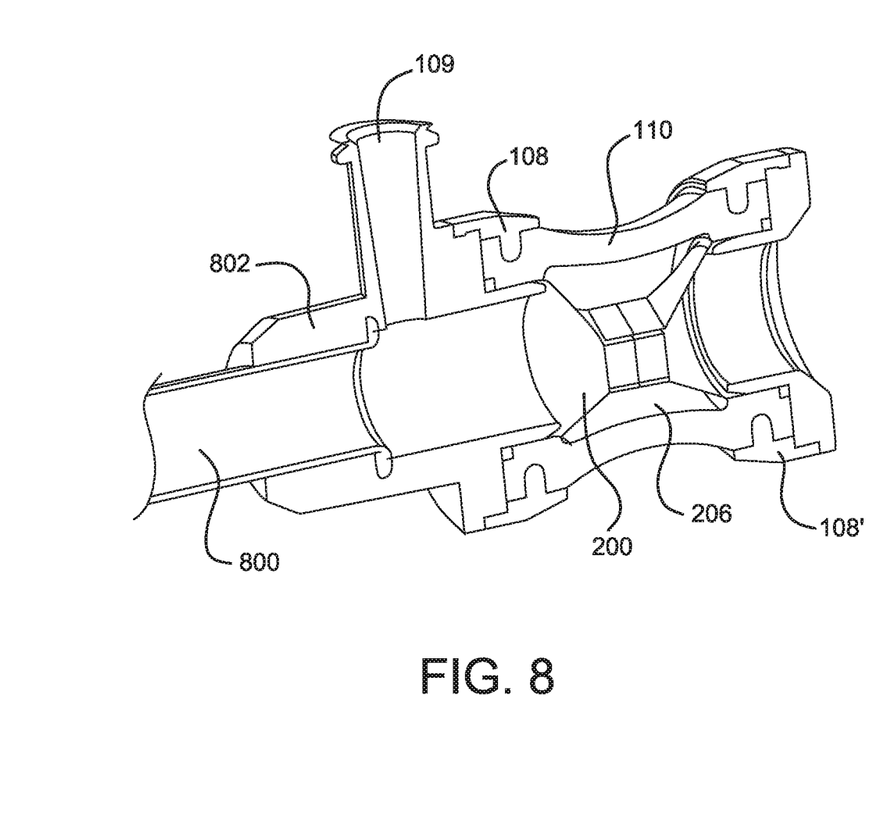
FIG. 8 is a cut away view of an introducer sheath which carries one embodiment of the introducer sheath valve.

FIG. 8 illustrates another embodiment of the invention. A sheath 800 similar to sheath 102 is attached to front fitting 802. Sheath 800 may be of similar dimension and material as that of sheath 102 but is constructed with a cuff at the proximal most end. Front fitting 802 may then be formed around or attached to sheath 800. Attachment methods are well known in the art and may include adhesive or insert molding. Front fitting 802 may be formed of similar materials to that of front fitting 106. Front fitting will be recognized to have similar features and advantages as that of front fitting 106 including gripping protrusion 107 (not shown) and flush port 109 with fitting. Snap ring 108, outer tube 110, inner tube 200 and pressurizable space 206 have been previously described in detail. Rear snap ring 108' is constructed of materials similar to that of snap ring 108' with fill port 112 and has features similar to that of snap ring 108' with fill port 112. Rear snap ring 804 may have a featured fill port but preferably does not include a fill port. Pressurizable space 206 may be filled upon assembly utilizing a specialized apparatus. Filling materials have been described previously.

EXAMPLES

Without intending to limit the scope of the invention, the following examples illustrate how various embodiments of the invention may be made and/or used.

Example 1

An introducer sheath valve assembly similar to FIG. 1 was manufactured using the following components and assembly process:

Components were fabricated using a rapid prototyping, stereolithography (SLA) process. The parts were fabricated by ProtoCam (Northampton, Pa.) using an SLA material designated as Accura® 25 plastic. This material when cured had an advertised tensile strength of about 38 Mpa, a tensile modulus of about 1590-1660 Mpa, an elongation to break of about 13-20% and a hardness of about 80 Shore D. The tensile and elongation data were derived using test method ASTM D 638. Five parts were fabricated using this SLA process and Accura® 25 plastic material. The parts included a threaded adapter, front fitting, snap ring with fill port, and a rear fitting.

Other materials required for the assembly of the introducer sheath valve were purchased items. A silicone o-ring having a round cross sectional shape with an outer diameter of about 14 mm, an inner diameter of about 12 mm, and a width of about 1 mm was procured from McMaster-Carr (Santa Fe Springs, Calif.). FEP rings were fabricated and cut to have an outer diameter of about 12.7 mm (0.475 inches), an inner diameter of about 10.5 mm (0.415 inches), and a thickness of about 0.76 mm (0.030 inches). FEP sheet used to fabricate the rings was procured from Saint-Gobain (Hoosick Falls, N.Y.). The outer tube was manufactured using a mold making rubber for prototype designs, Silastic® T-4 Base/Curing Agent, which was ordered from Dow Corning (K. R. Anderson, Inc. Morgan Hill, Calif.). The material when cured had an advertized tensile strength of about 970 psi, a tear strength of about 150 ppi, a hardness of about 40 Shore D, and an elongation at break of about 390%. The tear strength data was derived using test method ISO 34. Sheaths used for the construction of this device were either FEP or extruded high-density polyethylene with outer diameters ranging from about 7.52 mm to 7.70 mm, and inner diameters ranging from about 6.71 mm to 5.76 mm and were obtained from various suppliers. Polyvinyl chloride (PVC) tubing having an outer diameter of about 2.7 mm (0.107 inches), an inner diameter of about 1.7 mm (0.068 inches), and a length of about 19.05 cm was obtained from in house stock. A stainless steel mandrel (used to construct the inner tube) having a diameter of about 11.0 mm and a length of about 304.8 mm was supplied from in-house stock. A three way polycarbonate stop cock valve with a standard luer fitting was supplied from in-house stock. A quick set cyanoacrylate adhesive and a two part polyurethane adhesive were supplied from in-house stock. A Sharpie® fine point permanent marker was procured from in-house stock.

The introducer sheath valve was then assembled using the components described above. For the sheath assembly the non-threaded end of the threaded adapter was glued onto the proximal end of the sheath using a two part polyurethane adhesive. The silicone o-ring was then placed in a groove on the threaded end of the threaded adapter.

For the outer tube assembly, an hourglass shaped silicone tube (outer tube) was insert molded using Silastic® T-4 around the snap ring with fill port. The Silastic® T-4 was mixed per manufacturer's instructions, degassed as commonly known in the art, and poured into a custom two part mold housing the snap ring with fill port and the snap ring with fill port and cured. Curing time was a minimum of about 1 hour at about 75 degrees Celsius. Insert molding was performed in-house as commonly known in the art. The outer tube assembly was then removed from the mold and flash removed. The final outer tube dimensions were a tube wall thickness of about 2.7 mm, a largest outer diameter of about 17.8 mm, and a smallest outer diameter (at the smallest portion of the hourglass shape) of about 12.75 mm and a length of about 22.5 mm.

The inner tube assembly was then constructed using a thin porous ePTFE membrane. The thin porous ePTFE membrane was constructed as per U.S. Patent Publication No. 2007/0012624 A1 or U.S. Patent Publication No. 2008/0053892 A1. The thin porous membrane was rolled onto the stainless steel mandrel for five complete wraps then cut. On the same roll, a thin membrane produced according to the teachings of U.S. Pat. No. 7,049,380 was rolled for two complete wraps then cut. The thin porous ePTFE membrane was then rolled for another five complete wraps then cut. The final thickness of the construct was about 30 microns. FEP rings were then manually stretched over a Sharpie® fine point permanent marker, removed from the marker and placed on the wrapped tube construct at about 32.5 mm inner ring to inner ring intervals. The assembly was then placed in an ESPEC laboratory oven (model number STPH-201) at about 320 degrees Celsius for about 14 minutes. The assembly was then removed from the oven and allowed to cool to room temperature. The assembly was then stripped off the mandrel and segments were cut to include two FEP rings per segment.

The inner tube assembly was then inserted through the outer tube assembly such that the FEP rings extended from each end of the outer tube assembly. The FEP ring on the snap ring with fill port side was fitted over the protruding diameter of the front fitting. Cyanoacrylate adhesive was applied to the inner surface of the snap ring. The front fitting and the outer tube assembly were snapped together by hand. The remaining FEP ring was fitted over the protruding diameter of the rear fitting. Cyanoacrylate adhesive was applied to the inner surface of the snap ring with fill port and the rear fitting and snap ring with fill port were snapped together by hand.

The valve assembly was then threaded onto the sheath assembly. The PVC tubing was adhered to the fill port with cyanoacrylate adhesive and a three way stopcock valve was attached to the end of the tubing. The pressurizable space between the outer tube and the inner tube was pressurized through the stopcock valve to the desired pressure before testing using a syringe filled with water.

This example of the introducer sheath valve may be provided in a prefilled configuration by pressurizing the space between the outer tube and the inner tube and then using a plug or plugging substance to occlude the fill port.

Example 2

An introducer sheath valve assembly similar to FIG. 8 was manufactured using the following components and assembly process:

The parts were fabricated by ProtoCam (Northampton, Pa.) using an SLA material designated as Accura® 25 plastic. This material when cured had an advertised tensile strength of about 38 Mpa, a tensile modulus of about 1590-1660 Mpa, an elongation to break of about 13-20% and a hardness of about 80 Shore D. The tensile and elongation data were derived using test method ASTM D 638. Three parts were fabricated using this SLA process and Accura® 25 plastic material. The parts included two snap rings and a rear fitting.

Other materials required for the assembly of the introducer sheath valve were purchased items. The front fitting was manufactured in-house using a urethane plastic for prototype designs, Smooth-Cast® 300 urethane, which was ordered from ProtoCam (Northampton, Pa.). This material when cured had an advertised tensile strength of about 3,000 psi and a hardness of about 70 Shore D. A silicone o-ring having a round cross sectional shape with an outer diameter of about 14 mm, an inner diameter of about 12 mm, and a width of about 1 mm was procured from McMaster-Carr (Santa Fe Springs, Calif.). FEP rings were fabricated in house and cut to have an outer diameter of about 12.7 mm (0.475 inches), an inner diameter of about 10.5 mm (0.415 inches), and a thickness of about 0.76 mm (0.030 inches). FEP sheet used to fabricate the rings was procured from Saint-Gobain (Hoosick Falls, N.Y.). The outer tube was manufactured in-house using a mold making rubber for prototype designs, Silastic® T-4 Base/Curing Agent, which was ordered from Dow Corning (K. R. Anderson, Inc., Morgan Hill, Calif.). The material when cured had an advertized tensile strength of about 970 psi, a tear strength of about 150 ppi, a hardness of about 40 Shore D, and an elongation at break of about 390%. The tear strength data was derived using test method ISO 34. The sheaths used for the construction of this device was extruded high-density polyethylene with outer diameters ranging from about 7.52 mm to 7.70 mm, and inner diameters ranging from about 6.71 mm to 5.76 mm and was procured from in-house stock. A stainless steel mandrel (used to construct the inner tube) having a diameter of about 11.0 mm and a length of about 304.8 mm was supplied from in-house stock. A quick set cyanoacrylate adhesive and a two part polyurethane adhesive were supplied from in-house stock. A Sharpie® fine point permanent marker was procured from in-house stock.

The introducer sheath valve was then assembled using the components described above. To make the sheath assembly, the polyethylene sheath was RF (radio frequency) formed to create a cuff at the proximal most end. The cuff was approximately 0.94 mm thick and had an outer diameter 8.59 mm. The front fitting was insert molded over the cuff on the sheath using Smooth-Cast® 300 urethane. Smooth-Cast® 300 was mixed per manufacture's instructions and poured into a custom two-part mold. Insert molding was performed in-house as commonly known in the art. The assembly was then removed from the mold and flash removed.

For the outer tube assembly, an hourglass shaped silicone tube (outer tube) was molded using Silastic® T-4 silicone. The Silastic® T-4 was mixed per manufacture's instructions, degassed as commonly known in the arts, and poured into a custom two-part mold and cured. Curing time was a minimum of about 1 hour at about 75 degrees Celsius. Insert molding was performed in-house as commonly known in the art. The outer tube was then removed from the mold and flash removed. The final outer tube dimensions were a tube wall thickness of about 2.7 mm, a largest outer diameter of about 17.8 mm, and a smallest outer diameter (at the smallest portion of the hourglass shape) of about 12.75 mm and a length of about 22.5 mm. The snap rings were snapped onto the ends of the silicone tube. The silicone tube edges were lifted and a cyanoacrylate adhesive was applied between the edge of the silicone tube and the snap ring. The assembly was then placed at room temperature until the adhesive was fully cured according to manufacturer's instructions.

The inner tube assembly was made according to the method described in Example 1.

The inner tube assembly was then inserted through the outer tube assembly such that the FEP rings extended from each end of the outer tube assembly. Cyanoacrylate adhesive was then applied to the protruding diameter of the front fitting on the sheath assembly and the FEP ring was fit over the protruding diameter of the front fitting. Cyanoacrylate adhesive was applied to the inner surface of a snap ring on the outer tube assembly. The front fitting and outer tube assembly were snapped together by hand. Cyanoacrylate adhesive was applied at the base of the protruding diameter of the rear fitting. The remaining FEP ring was fitted over the protruding diameter of the rear fitting.

The pressurizable space between the outer tube and the inner tube was then pressurized with glycerin. In order to pressurize the space with glycerin, the valve assembly was placed in an in-house made fixture. The fixture consisted of a movable housing to grasp the rear fitting and a stationary housing to grasp the snap ring and outer tube assembly. This fixture maintained a gap of approximately 2.0 mm between the rear fitting and the snap ring during pressurizing. The fixture also consisted of a cuff containing two o-rings on its interior with a diameter designed to form a tight seal around the rear fitting and the snap ring. The cuff was fitted with an aperture extending through the cuff and a tube connected to the aperture. The tube was connected to a syringe filled with glycerin. The cuff was fitted over the gap between the rear fitting and the snap ring and the pressurizable space was filled with glycerin to the desired pressure. Once the space was filled, and while the cuff was still fitted over the gap between the rear fitting and the snap ring, the movable housing was pushed toward the snap ring to close the gap. Excess glycerin was removed from the outside of the introducer sheath valve assembly.

While particular embodiments of the present invention have been illustrated and described herein, the present invention should not be limited to such illustrations and descriptions. It should be apparent that changes and modifications may be incorporated and embodied as part of the present invention within the scope of the following claims.

What is claimed is:

1. An introducer sheath valve comprising:
   an outer tube having an hourglass shape and formed of an elastomeric material;
   an inner tube having a thickness between about 0.0025 mm to about 1 mm; and
   a pressurizable space formed between an inner surface of the outer tube and an outer surface of the inner tube, the outer tube configured to distend from the hourglass shape to provide a visual indicator of pressurization and the inner tube configured to collapse to form a seal for preventing back-bleeding through the seal when the pressurizable space is pressurized.

2. The introducer sheath valve of claim 1, wherein the inner tube comprises a lubricious material.

3. The introducer sheath valve of claim 1, wherein the inner tube comprises a material selected from the group consisting of ePTFE (expanded polytetrafluoroethylene), fabrics, silk, and Kevlar®.

4. The introducer sheath valve of claim 3, wherein the inner tube comprises ePTFE.

5. The introducer sheath valve of claim 1, wherein the pressurizable space is formed by sealing a first end of the outer tube to a first end of the inner tube and sealing a second end of the outer tube to a second end of the inner tube.

6. The introducer sheath valve of claim 5, wherein the sealing is accomplished by at least one of the following: interference fit, adhesion, thermal bond, and insert molding.

7. The introducer sheath valve of claim 6, wherein the interference fit is formed using at least one o-ring.

8. The introducer sheath valve of claim 1, wherein the pressurizable space maintains a pressure wherein the pressure is attained by an external source.

9. The introducer sheath of claim 8, where in the pressure is attained by at least one of the following: finger pressure, a leaf spring, and filled syringe.

10. The introducer sheath valve of claim 1, wherein the inner tube comprises a polymer.

11. The introducer sheath valve of claim 10, further comprising at least one polymer filling at least a portion of the inner tube.

12. The introducer sheath valve of claim 1, further comprising at least one polymer filling at least a portion of the inner tube.

* * * * *